United States Patent [19]

Bryant et al.

[11] Patent Number: 5,578,995
[45] Date of Patent: Nov. 26, 1996

[54] METHOD OF MONITORING AND CONTROLLING CONDENSATE QUALITY

[75] Inventors: Robert L. Bryant, DeKalb County; Charles R. Veal, Gwinnett County, both of Ga.

[73] Assignee: Chemtrac Systems, Inc., Norcross, Ga.

[21] Appl. No.: 187,397

[22] Filed: Jan. 25, 1994

[51] Int. Cl.⁶ .................................................. G08B 21/00
[52] U.S. Cl. ........................ 340/627; 250/573; 250/574; 356/37; 356/338; 356/339; 356/442
[58] Field of Search ........................... 340/627; 250/573, 250/574, 577; 122/4 R; 356/37, 338, 339, 442

[56] References Cited

U.S. PATENT DOCUMENTS

| | | | |
|---|---|---|---|
| 2,684,008 | 7/1954 | Vonnegut | 356/37 |
| 3,694,085 | 9/1972 | Rich | 356/37 |
| 3,806,248 | 4/1974 | Sinclair | 356/37 |
| 3,976,541 | 8/1976 | Stiteler et al. | 176/37 |
| 4,449,816 | 5/1984 | Kohsaka et al. | 356/37 |
| 4,639,718 | 1/1987 | Gasper | 340/603 |
| 5,026,155 | 6/1991 | Ockovic et al. | 356/37 |
| 5,118,959 | 6/1992 | Caldow et al. | 250/573 |

FOREIGN PATENT DOCUMENTS 2129549  3/1986  United Kingdom.

OTHER PUBLICATIONS

ChemTrac Systems, Inc., Precise Water Treatment Control, Dynamic Light Obscuration–DLO, PM 2500.

*Primary Examiner*—Jeffery Hofsass
*Assistant Examiner*—Julie B. Lieu
*Attorney, Agent, or Firm*—Vivian L. Steadman; Harry I. Leon

[57] ABSTRACT

An improved method of monitoring condensate quality in a condensate return system and of controlling the level of particulate matter in the condensate flow so that when this level exceeds an acceptable limit, valves for discharging the condensate flow from the system open automatically or, alternately, an alarm is sounded. Utilization of the method facilitates the conservation of hot steam condensate for reuse in a boiler while preventing water contaminated with particulate matter from returning to the boiler, thereby protecting it from certain types of deposits and corrosion. The improved method includes measuring, on a continuous basis, relative numbers of particulate-type impurities under conditions in which rust or other particles large enough to block flow into a particle counter can be produced in sudden surges. Tests show that a suitable instrument for measuring the impurities under such conditions is a particle monitor. In the improved method, the only restriction on the size of the particles to be monitored is that the particles be small enough to pass through vinyl tubing having an inner diameter of about 3 millimeters.

2 Claims, 7 Drawing Sheets

METHOD OF MONITORING AND CONTROLLING CONDENSATE QUALITY

BACKGROUND OF THE INVENTION

Ideally, the water in a boiler feedwater/steam condensate return system is free of both dissolved and particulate matter. Even low levels of certain contaminants, if present in the condensate, can be detrimental to plant performance, resulting in reduced efficiency, production loss and plant shutdowns.

Unlike raw water, steam condensate is introduced into boiler feedwater/steam condensate return systems at temperatures well above ambient. Recognizing that substantial quantities of energy can be saved by recycling hot condensate, plant engineers have sought, for processes utilizing steam, to maximize the heat content and quantity of condensate returned to the boiler. Increasingly, these engineers are using condensate formed during startup and as production rates are adjusted, even though such activities can result in surges in the concentrations of impurities present in the condensate. If sent to a boiler, these surges can lead to increased fouling and higher rates of boiler tube failure.

One of the most undesirable contaminants in condensate is iron oxide. Not only is iron oxide difficult to treat chemically once it enters the boiler but also this substance has a great affinity for forming deposits within boiler tubes in high heat flux areas. Such deposits of iron oxide cannot easily be removed on-line. Generally, acid must be used to remove these deposits and to insure continued boiler reliability.

Produced by the natural forces of erosion and of corrosion acting within each steam/condensate system, iron oxide is inherently formed with condensate. Attempts, whether using mechanical or chemical means, to minimize the formation of iron oxide are at best imperfect. In addition to startups and shutdowns of plant processes, situations which can contribute to iron oxide being present in unacceptably high concentrations are: an inadequate or poorly controlled condensate treatment program; cross-contamination of condensate with process chemicals; and malfunctioning of equipment employed to pretreat boiler feedwater.

In most plants, normal operating practice has been to send contaminated condensate to the sewer. Unfortunately, deciding when one should open dump valves to release contaminated condensate has been fraught with uncertainty. Plant operators have not had a simple and reliable method at their disposal for continuously monitoring condensate contaminants and iron oxide in particular. Unfortunately, traditional condensate monitoring techniques, which rely on conductivity and pH measurements, do not provide an accurate indication of the concentrations of insoluble impurities such as iron oxide. Insoluble hardness levels, for example, can be excessive even though soluble hardness levels are below detection limits.

As for measuring iron oxide concentrations, many plant operators still rely upon a grab sample method of analysis which was developed about 30 years ago by the Babcock Wilcox Company. In this analysis, one basses a 1-liter sample through a 0.45 micron membrane filter and then compares the appearance (color, darkness and the like) of the filter bad with known "standards". Since the appearance of the filter bad can vary with, among other things, when and how the operator takes the sample and the analyst's interpretation of the experimental results, plant operators, depending upon such analyses, can easily find themselves underfeeding or overfeeding corrosion control chemical(s).

While more precise measurements based on chemical analysis of iron oxide concentrations can be performed, such measurements cannot, as a practical matter, be performed on-line. Photometric methods, for example, are encumbered by the fact that time-consuming acid digestion is required to convert ferric iron to soluble ferrous iron. Similarly, precision measurements based on atomic adsorption necessitate costly time delays. These measurements must be obtained using extremely expensive test equipment. Because such equipment is not suitable for most plant environments, samples usually must be transported off-site. Several days may pass before results are known, making the data useless to operators who must make decisions quickly to protect a system.

To provide an on-line analysis of condensate quality, some plants monitor for particulate matter, but not for iron oxide concentration. This approach is of value because, ordinarily, the level of particulate matter is indicative of the level of iron oxide, a major component of this particulate matter. In the past, turbidimeters have been used to obtain surrogate measurements for particulate iron in condensate.

Turbidimeters, however, measure turbidity rather than the actual numbers or concentration of particles. Turbidity, an expression of the optical property that causes light to be scattered and absorbed rather than transmitted in straight lines through an aqueous sample, is affected by the size, shape and composition of particles in the sample. Importantly, for a sample of unit volume having a given mass of particles, the turbidity is less when the particles are larger in size. As a consequence, relatively large particles can be present in a sample but not contribute much to its measured turbidity.

Moreover, several conditions affecting the optical surfaces of the walls of the sample cell can interfere with the accuracy of a turbidimeter. These surfaces may be imperfect due to the presence of dust, scratches, smudges, condensate or, especially in the case of continuous sampling units, an accumulated film formed thereon. While film formation can be abated with regular cleaning of the cell, fogging of the cell walls is a persistent source of interference when flows at elevated temperatures, such as steam condensate flows, are monitored.

Instruments known as particle counters, which are capable of sizing as well as counting particles, can be employed to overcome some of the limitations of turbidimeters. Accurate particle counting, however, is limited to those situations in which the concentrations of particles are low enough to avoid coincidence effects caused by the simultaneous passage of two or more particles through the sensing zone of the particle counter.

In practice, particle counters utilize narrow, gate-like sieves in a technique known as hydrodynamic focusing to minimize coincidence effects. Typically, these sieves allow only particles which are about 65 microns or smaller in size to pass through them. As long as all of the particles are small enough to pass through the sieve upstream of each particle counter in a system, plugging is prevented. When a flow blockage occurs, however, the instrument gives an erroneously low particulate matter concentration. This error arises because in particle counting, it is automatically assumed that the flow rate through the sensing zone of the counter remains constant and that the output of the counter is inversely proportional to this fixed flow rate even when the flow rate drops precipitously.

Partly as a result of particle size limitations, particle counters have not found utility in the steam condensate field but rather are used primarily for monitoring filtered water in the potable water treatment field. Unlike condensate which may contain large rust particles, filtered water has mainly small particles and very few or no particles greater than 20 microns in size.

Even in the potable water field, acceptance of particle counters has not been widespread. Utilities have been slow to adopt them because of their cost, operators' lack of familiarity with the instrument, and the tremendous, even excessive, amount of detailed information which particle counters generate. Turbidity measurement has remained the standard method of determining the efficiency of clarification and filtration processes in removing particles from raw water.

An alternative method developed for the on-line monitoring of concentrations of particles in water involves the use of an apparatus described by Gregory add Nelson in U.K. Patent GB 2,129,549B known as a particle monitor. The sensitivity of the particle monitor, like that of the particle counter, is dependent upon the size of particles being measured. For very small, colloidal particles, turbidimeters give better detection than particle monitors. For particles larger than 2.0 microns, the particle monitor has a detection capability 100 times greater than that of a turbidimeter and can be used to detect sub-ppb of such particles.

Instead of providing, as does the particle counter, counts of particles within several size ranges, the particle monitor has an output which is limited to a single number known as a particle index. This difference is due to the fact that the particle monitor utilizes an averaging technique in which a ratio is measured between fluctuations in the instantaneous intensity and the average intensity of a light or infrared radiation beam transmitted through a suspension flowing through a transparent plastic tube. As a particle passes between the light source and the detector, a shadow is created, causing a fluctuation. Importantly, measurement of these fluctuations eliminates the need for hydrodynamic focusing or a like technique to avoid coincidence effects.

SUMMARY OF THE INVENTION

The object of the present invention is to provide an improved method of monitoring condensate quality in a condensate return system and of controlling automatic dumping of the condensate flow when the level of particulate matter therein exceeds an acceptable limit. Utilization of the method facilitates the conservation of steam condensate for reuse in a boiler while preventing water contaminated with particulate matter from returning to the boiler, thereby protecting the boiler from deposition of iron oxide within its tubes and certain other types of corrosion.

Alternately, the object of the present invention is to provide an improved method of monitoring condensate quality in a condensate return system and of signaling an alarm when the level of particulate matter therein exceeds an acceptable limit.

A further object of the present invention is to provide an improved method of maintaining the purity of boiler feedwater in a steam/condensate system in which not only is the best quality water supplied as makeup water for the boiler but also as much condensate as possible is recirculated to the boiler.

The improved method includes the steps of continuously monitoring a portion of the condensate flow; measuring, on-line, relative numbers of particles in the condensate flow over a wide range of concentrations; and signaling an alarm or, alternately, a controller to actuate means for diverting the condensate flow when the relative number of particles in the condensate flow exceeds a preset value.

DETAILED DESCRIPTION OF THE INVENTION

The improved method according to the present invention comprises monitoring condensate quality in a steam condensate return system and controlling automatic dumping of the condensate flow when the concentration of particulate matter therein exceeds an acceptable limit. Alternately, the method includes signalling an alarm when the acceptable limit is exceeded.

In the improved method, a small sidestream of the condensate flow is continuously directed through a flexible, transparent tube fluidly connected to the steam condensate return system. A section of this tube is mounted within a particle monitor so that, in operation, a portion of the sidestream traverses an intense light beam generated, within the particle monitor, by a light emitting diode (LED) and directed perpendicularly to the sidestream flow. Variations in the particulate matter present in this portion of the sidestream produce fluctuations in the intensity of the light beam which are sensed by a photodetector within the particle monitor. The fluctuations give rise to a fluctuating electronic signal in the output of the photodetector; and this signal is then analyzed, by segments, corresponding to fixed intervals of time, to obtain a measure of particulate matter concentrations in the condensate flow over these same time intervals.

Limits on the concentrations of contaminants in steam condensate and in feedwater have been suggested by the Industrial Subcommittee of the American Society of Mechanical Engineers (ASME) Research Committee on Water in Thermal Power Systems. These limits were intended to improve steam equipment reliability by retarding corrosion, minimizing deposit formation and improving steam purity. The suggested ASME water quality limits for an industrial watertube, drum-type boiler with superheater, turbine drives or process restrictions on steam purity are given in Table A below. These limits vary with the contaminant but generally decrease in magnitude as the operating pressure of the boiler increases.

TABLE A

Suggested Water Quality Limits
Boiler Type: Industrial, Drum-Type
Watertube Boiler

| Drum Pressure | Feedwater Total Iron, mg/liter Fe | Boiler Water | | | |
|---|---|---|---|---|---|
| | | Silica, mg/liter $SiO_2$ | Total Alkalinity, mg/liter $CaCO_3$ | Free Hydroxide Alkalinity, mg/liter $CaCO_3$ | Specific Conductance, microS/cm at 25 deg C. without Neutralization |
| 0–300 | 0.100 | 150 | <350 | NS | <3,500 |
| 301–450 | 0.050 | 90 | <300 | NS | <3,000 |
| 451–600 | 0.030 | 40 | <250 | NS | <2,500 |
| 601–750 | 0.025 | 30 | <200 | NS | <2,000 |
| 751–900 | 0.020 | 20 | <150 | ND | <1,500 |
| 901–1000 | 0.020 | 8 | <100 | ND | <1,000 |
| 1001–1500 | 0.010 | 2 | NS | ND | 150 |

Condensate return systems, where this method can be used to advantage, are found in a wide range of industrial plants, including refineries, paper mills and chemical plants. These plants generally operate boilers at pressures not exceeding 1500 psig. Shown schematically in FIG. 1 is a typical layout for such a facility equipped for cogeneration.

Figure 1:
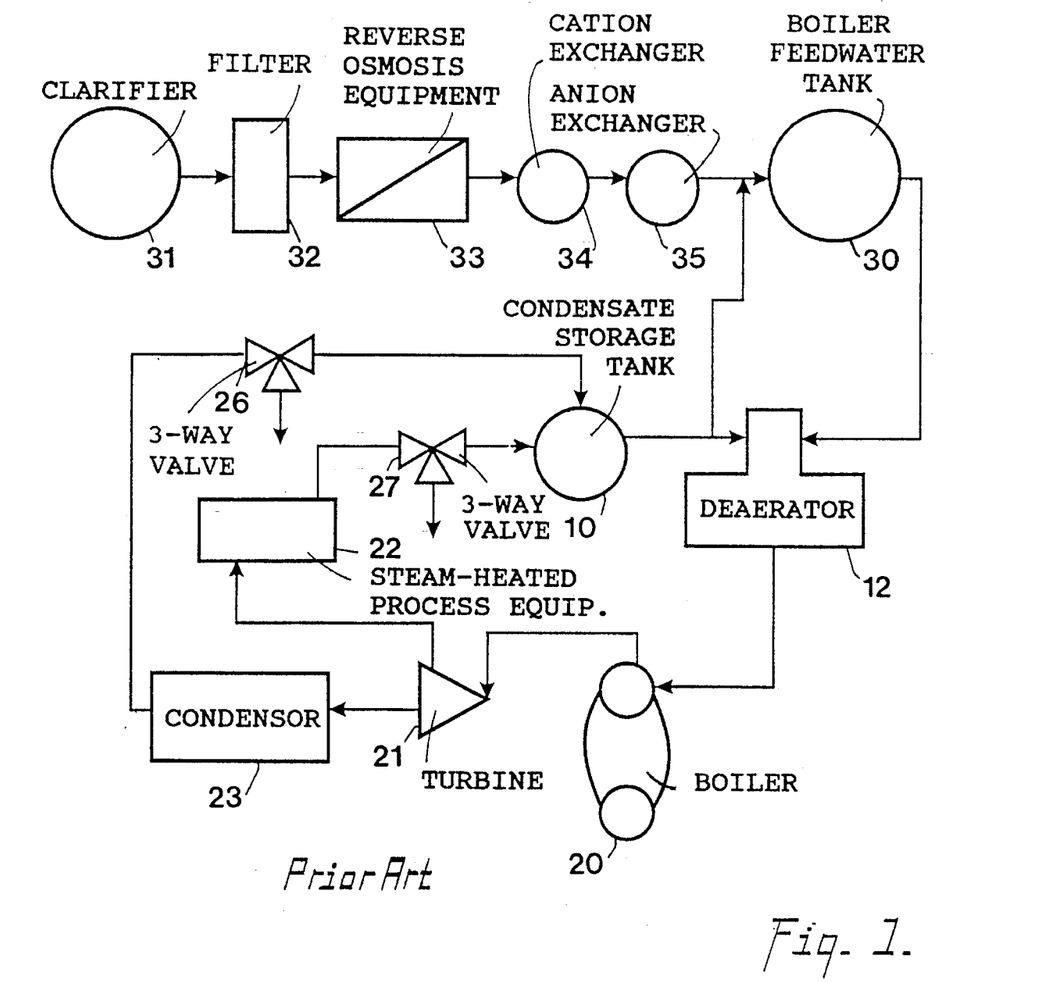
FIG. 1 is a schematic of a layout for a typical industrial cogeneration plant according to the prior art, the plant having a steam boiler fed both by recovered condensate and by filtered and demineralized raw water, the latter serving as makeup for steam/water lost during process operations.

As illustrated in FIG. 1, a condensate return system includes a condensate storage tank 10, a boiler feedwater tank 30, a deaerator 12, a boiler 20, a turbine 21, steam-heated process equipment 22 and a condensor 23. Steam generated by the boiler 20 drives a two-step turbine, which is part of the facility's power plant, and exits the turbine in two streams: steam at a higher temperature and steam at a lower temperature. The higher temperature steam is piped to heat exchangers (not shown) in the process equipment 22 where most of the heat content of the steam is transferred to materials undergoing processing. The lower temperature steam, on the other hand, is sent directly to a condensor 23. Downstream of the process equipment 22 and of the condensor 23, steam condensate is collected in the condensate storage tank 10. Makeup water, employed to compensate for any losses of steam and of condensate from the system, is then mixed with the condensate in a boiler feedwater tank 30. Unlike raw water, this makeup water has been highly purified, having been subjected to a series of pretreatment steps including, in sequence, the use of a clarifier 31, a filter 32, reverse osmosis equipment 33, and cation and anion exchangers 34 and 35, respectively. Circulation of the mixture of condensate and makeup water between the tank 30 and a deaerator 12 allows steam and other gases, such as oxygen, which are trapped in this water mixture to escape before the mixture is pumped to the boiler 20.

Figure 2:
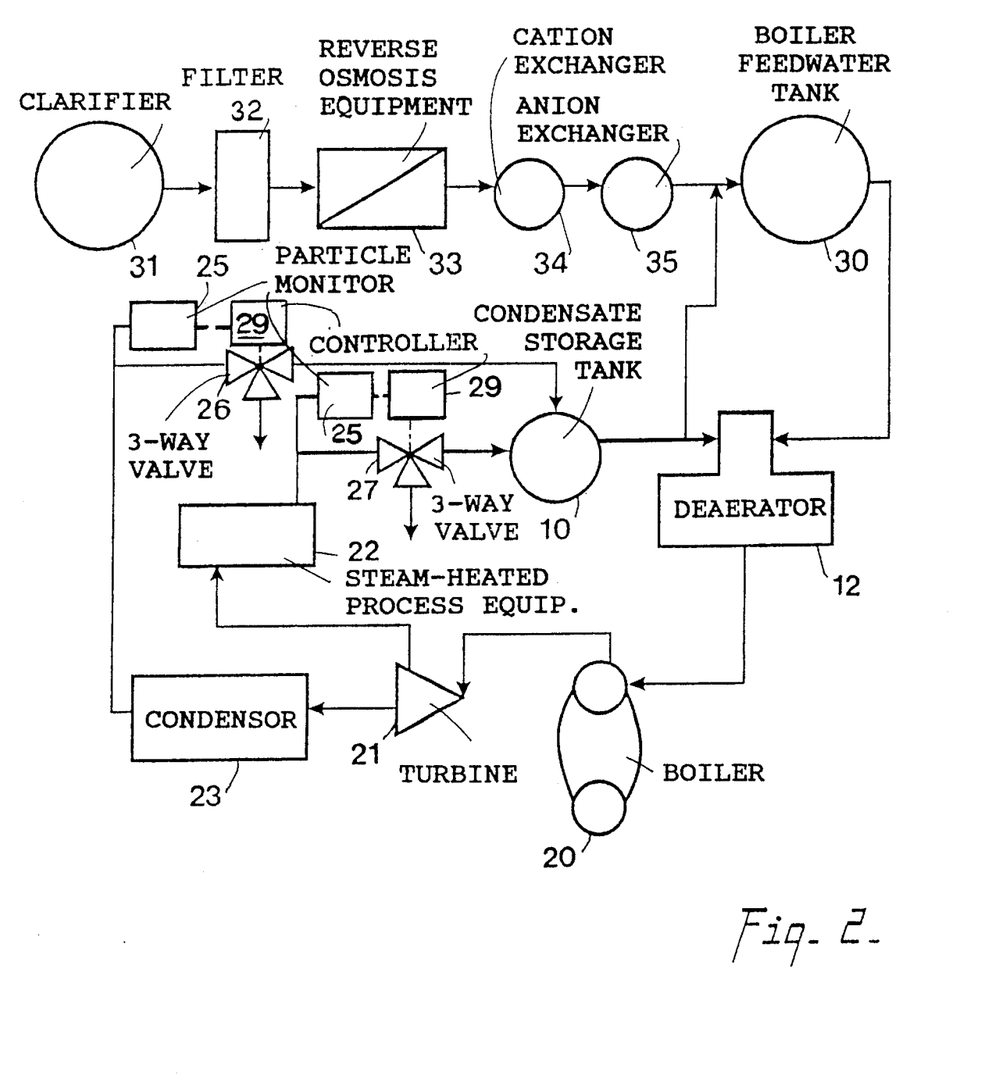
FIG. 2 is a schematic of the layout for the plant according to FIG. 1 modified to include a system for maintaining condensate quality in condensate flow intended for reuse in a boiler.

A similar cogeneration facility, but one also equipped with a system for maintaining condensate quality according to the improved method is shown schematically in FIG. 2. As illustrated in FIG. 2, 3-way valves 26, 27 are preferably located downstream of the condensor 23 and of the process equipment 22, respectively. A particle monitor, denoted generally by the reference numeral 25, is situated so that the monitor can sample the flow upstream of each 3-way valve. If a particle monitor 25 signals a sufficiently high concentration of particles in its respective condensate flow stream, a controller 29 electronically connected to the monitor actuates the corresponding valve 26, 27, dumping said condensate flow stream so that it can not be returned, without treatment, to the boiler 20.

Figure 3:
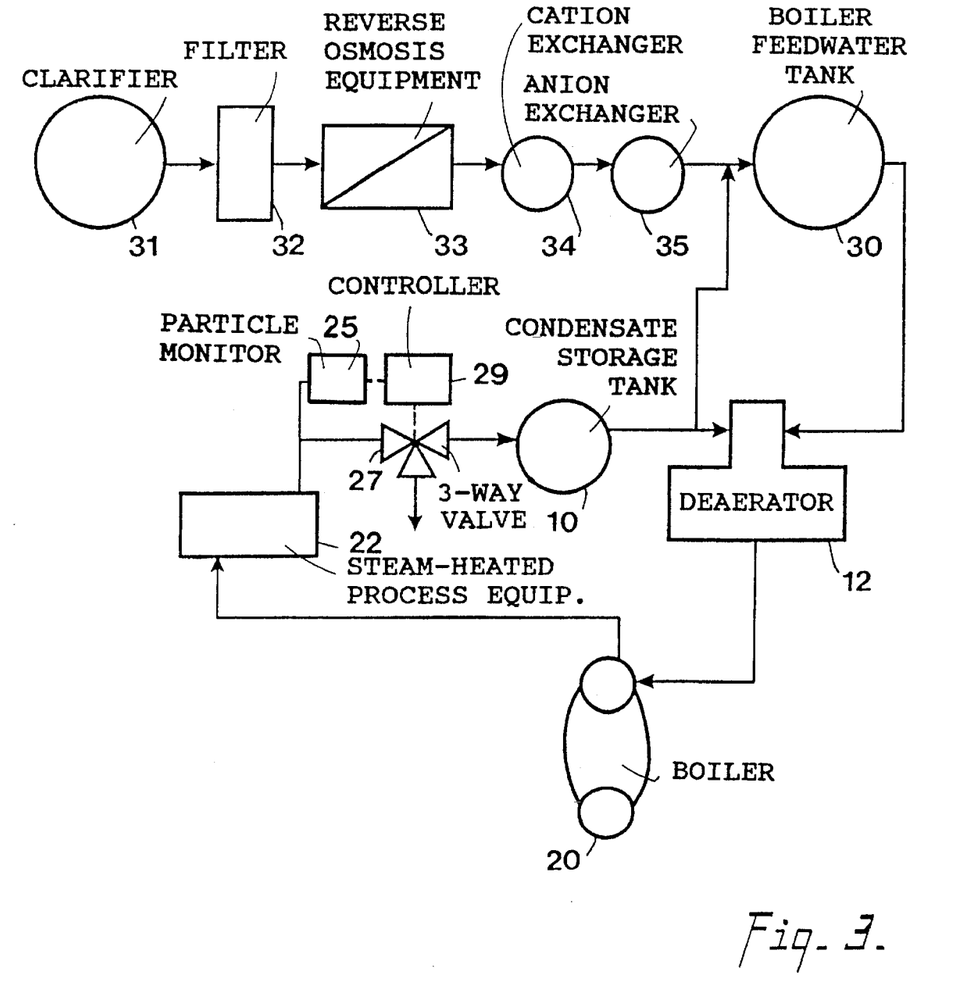
FIG. 3 is a schematic of a layout for an industrial plant lacking cogeneration but otherwise similar to the plant having a layout according to FIG. 2.

Another facility, also equipped with a system for maintaining condensate quality according to the improved method but lacking cogeneration, is shown schematically in FIG. 3. As illustrated in FIG. 3, a 3-way valve 27 is preferably located downstream of process equipment 22. A particle monitor 25 is situated so that the monitor can sample the flow upstream of the 3-way valve 27. If a particle monitor 25 signals a sufficiently high concentration of particles in the condensate flow stream, a controller 29 electronically connected to the monitor actuates the valve 27, dumping said condensate flow stream so that it cannot be returned, without treatment, to the boiler 20.

Figure 4:
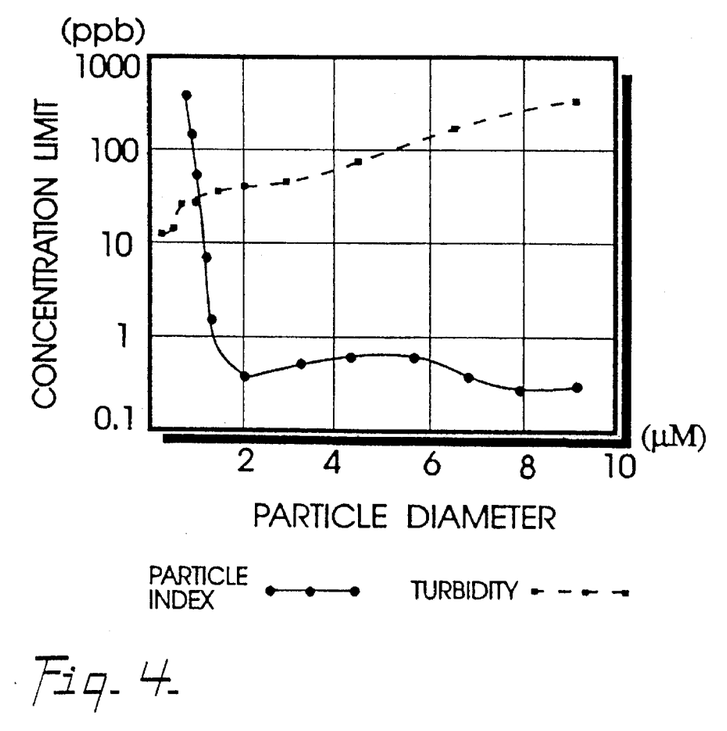
FIG. 4 is a graph comparing lower detection limits which are characteristic of particle monitors and of turbidimeters.
Figure 5:
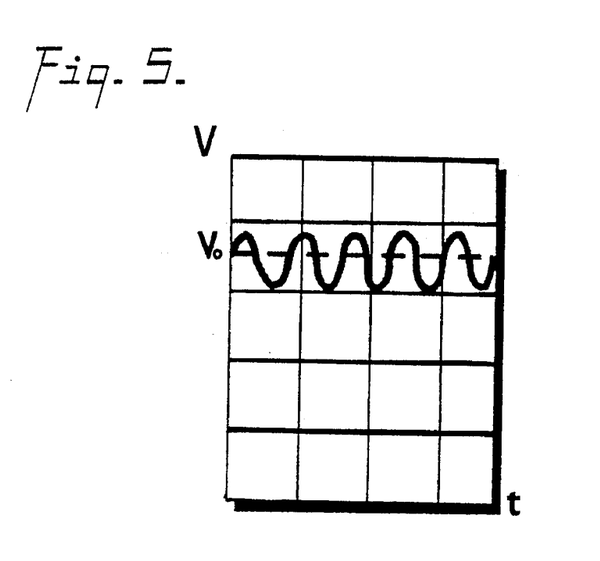
FIG. 5 is a typical plot of the output of the sensor in a particle monitor, the oscillating line on the plot showing the RMS AC component in volts as a function of time and the dashed line showing the D.C. component denoted as "Vo"

In FIGS. 2 and 3, the monitors 25 are instruments capable of measuring rust particle-size impurities in water and preferably provide a continuous output of the results of such measurements. For this application, Models PM 2500 and PM 3500 particle monitors, available commercially from Chemtrac Systems, Inc., of Norcross, Ga., have been found to be satisfactory. Characteristically, these instruments can detect the presence of 1 micron and larger particles. Lower detection limits and typical output for the sensor of the model PM 2500 particle monitor are shown in FIGS. 4 and 5, respectively.

Figure 6:
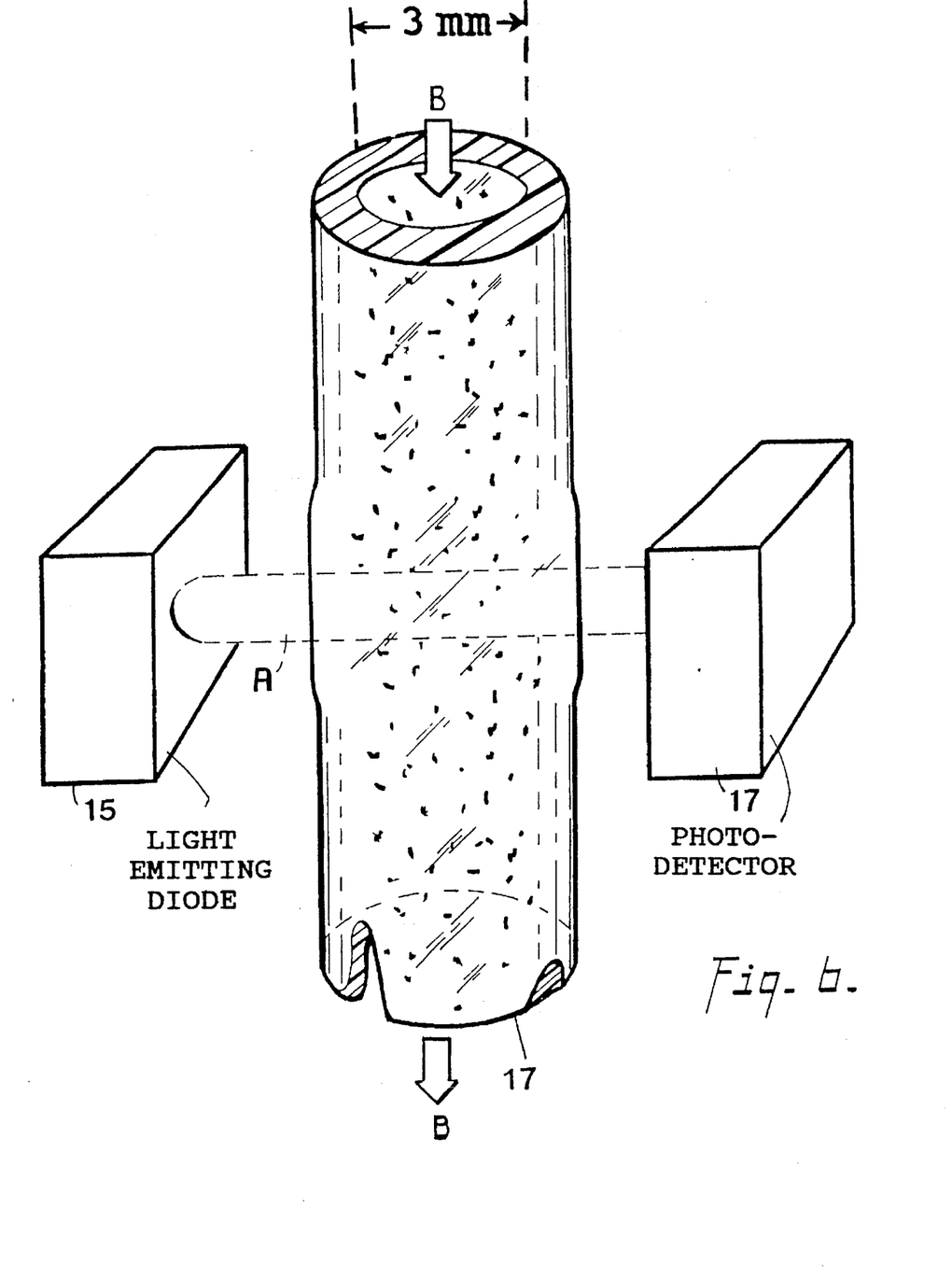
FIG. 6 is a schematic of components employed to practise an embodiment of the method according to the present invention, the components including sample tubing through which condensate flows and both a light emitting diode (LED) and a photodetector of a particle monitor, the LED generating a light beam which is partially, and momentarily, obscured by particulates in the condensate as they traverse the light beam.

As illustrated schematically in FIG. 6, particle monitors, such as the Model 2500 monitor, transmit a narrow infrared light beam A from a light emitting diode (LED) 15 to a photodetector 16. The light beam A is preferably about 0.4 mm wide, with a wavelength of around 850 nm, that is, just in the infrared. Before reaching the photodetector 16, the light beam A traverses a flexible, transparent plastic tube 17 as a portion of the condensate flow B moves through it. Preferably, the flow rate of the condensate in this tube 17, which, by way of example, is 3/16 inch OD vinyl tubing with an internal diameter of 3 mm, is 100 ml per minute.

A preferred particle monitor 25 for use with this method further includes means for holding the sample tube in such a way that the plastic tube, which is otherwise round in transverse cross-section, is generally flattened on the sides of the tube where it is traversed by the light beam, said sides of the tube being proximate with the light source and the photodetector, respectively. The flattening of these sides reduces reflection of the light beam from the walls of the tubing. Maintenance of the plastic tube is accomplished by simply replacing it. Prior to its replacement, as the plastic tube becomes gradually more discolored or coated, the monitor 25, preferably utilizing a sensor with a LED feedback circuit as is used in the models PM 2500 and PM 3500, automatically adjusts the average intensity of the light be traversing the tube so that this average intensity is maintained at a constant level at the photodetector.

In operation, particles in the condensate flow traversing the light beam momentarily block it, creating fluctuations in the intensity of the light reaching the photodetector. In response, the photodetector generates a fluctuating electronic signal which has two components: a D.C. component which corresponds to the average (mean) number of particles in the condensate flow and a fluctuating A.C. component. Because the particle monitor responds to fluctuations in the intensity, rather that to absolute intensity, the particle monitor ie not susceptible to electronic "drift" caused by noise, light source variances, optical surface fouling and fogging at elevated temperatures.

The root mean square of the A.C. component of the fluctuating electronic signal, once this component has been isolated and amplified, is then determined for a measurement time interval which, by way of example, is in the range of between 1 and 10 seconds. Finally, the ratio of the root mean square of the A.C. component to the D.C. component is manipulated mathematically to give a relative number known as the particle index, a number which is proportional to the square of this ratio. As may be show theoretically, the particle index is also proportional to the summation, over all particle sizes, of the product of the concentration of particles within a given size range multiplied by the square of the light scattering cross-section of that particular size range of particles.

In the improved method, the output of each particle monitor 25, which is limited to a single particle index over each measurement time interval, is compared, on-line and continuously, with a limiting particle index. For each condensate return system, a plant operator must empirically determine the limiting particle index for each particle monitor.

As a rule, limiting particle indices vary with the boiler operating pressure: the higher the operating pressure of an industrial, drum-type watertube boiler, the lower the limiting particle index for a given particle monitor. To indicate generally the values of limiting particle indices, particle indices were determined, using a Model PM 3500 particle monitor, for water samples containing iron oxide particles, in sizes ranging from 0.8 to 2 microns, at known concentrations. The results of these experiments are shown in Table B below. The iron oxide concentrations selected (0.025 and 0.100 mg/liter of total iron) were among the concentrations given as water quality limits for boiler feedwater in Table A hereinabove.

TABLE B

Measured Limiting Particle Indices
Boiler Type: Industrial, Drum-type Watertube Boiler

| Drum Operating Pressure (psig) | Feedwater Total Iron (mg/liter Fe) (from Table A) | Concentration of 0.8–2 Micron Iron Oxide Particles | | Limiting Particle Index (10 sec. Interval) |
|---|---|---|---|---|
| | | (ppb) | (particles/ml) | |
| 0–300 | 0.100 | 416 | 240 | 546 |
| 601–750 | 0.025 | 104 | 60 | 214 |

In actual applications, appropriate limiting particle indices corresponding to the iron oxide concentrations in Table A may differ from those shown in Table B. Among the factors contributing to such differences is the fact that iron oxide may constitute substantially less than 100 percent of the particulate matter content of the condensate. Moreover, the particles involved in a condensate flow are likely to vary in size over a much greater range than the 0.8 to 2 microns range of the particles whose concentrations are reported in Table B.

The limiting particle index for each condensate return system is preferably determined by simultaneously diverting a portion of the condensate flow through a particle monitor 25 and taking a sample of the condensate flow to determine the concentration of iron oxide therein using sophisticated analytical chemistry techniques, such as atomic absorption spectroscopy. When minor or major excursions from the average particle concentration of the condensate flow occur as evidenced by the particle monitor, additional samples of the condensate are preferably also collected and chemically analyzed. In this way, the operator determines what is the normal operating condition for the condensate return system at his plant and what conditions indicate excessive concentrations of iron oxide in the condensate flow. Once the limiting particle index has been determined using a monitor in a particular system, the monitor ordinarily does not need to be recalibrated for use in that system.

Figure 7:
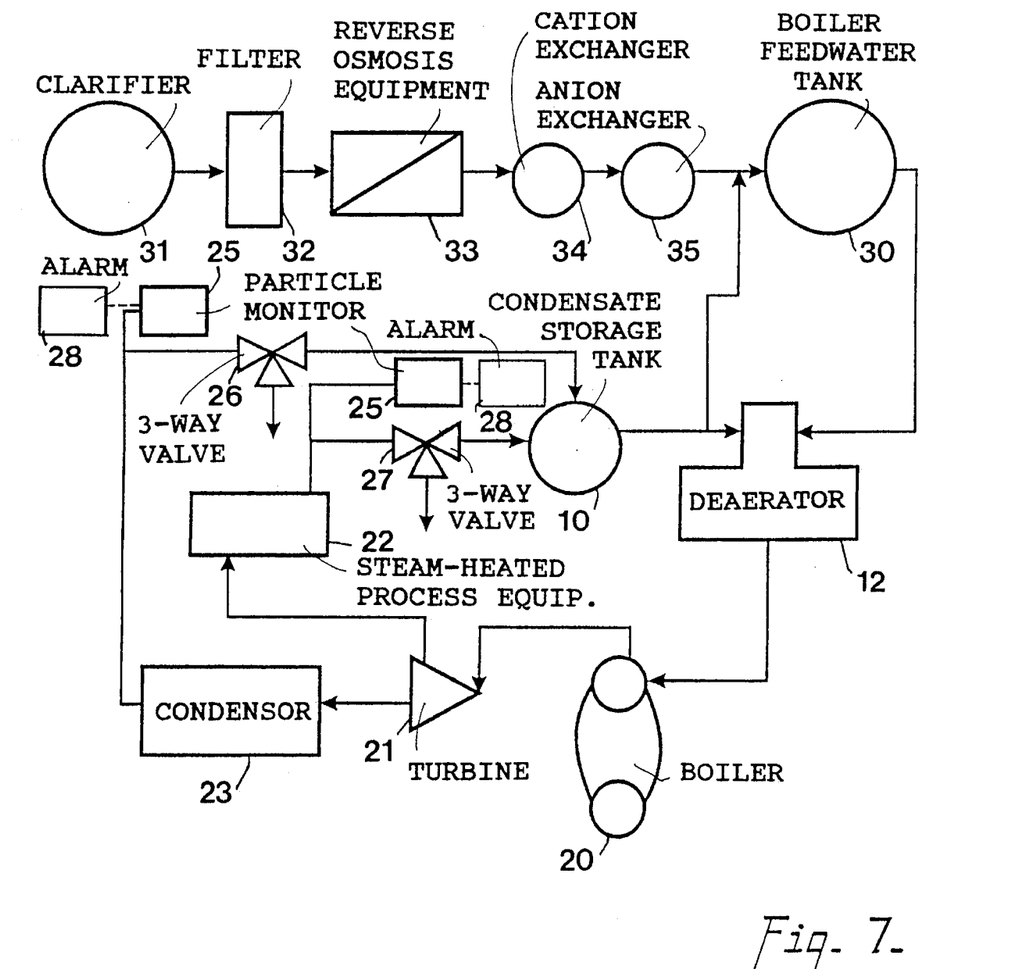
FIG. 7 is an alternate embodiment of the system shown schematically in FIG. 2.
Figure 8:
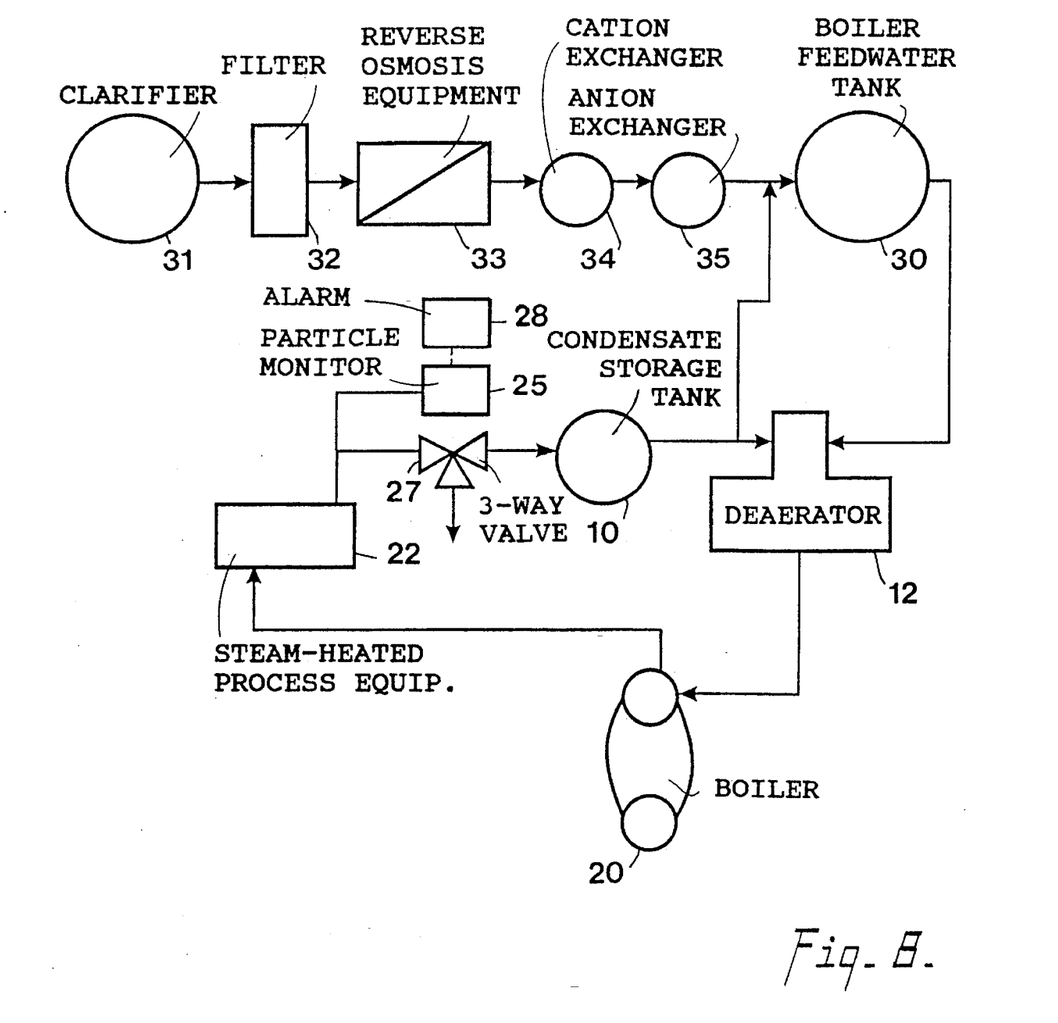
FIG. 8 is an alternate embodiment of the system shown schematically in FIG. 3.

In addition to measuring, on-line, particle indices representative of the relative numbers of one (1) micron or larger particles in the condensate flow, the improved method includes the steps of continuously monitoring condensate flows downstream of steam-driven process equipment 22 in a condensate return system and downstream of any condensor 23 for a steam turbine 21 in the system; and signalling a controller to actuate means for diverting any of these condensate flows when the relative number of particles therein exceeds the predetermined limiting particle index. Alternately, when this limiting index, as measured by a particle monitor upstream of either of the valves 26, 27, is exceeded, the monitor triggers an alarm (28 FIGS. 7 and 8). Further, any loss of boiler feedwater/condensate from the condensate return system must be compensated for by adding water, which has been purified to make it ultra pure.

In a further embodiment of the method, the monitor 25 also triggers an alarm when the monitor measures a particle index which corresponds to a minor excursion above normal values in the concentrations of particles in the condensate, so that the plant operator can determine the cause of the minor excursion and possibly reduce the number of incidences of such excursions. In an application in which the method was employed to monitor particle concentrations in a condensate stress in a paper mill, minor excursions in the particle index, indicative of higher iron concentrations, occurred for one hour periods following paper machine breaks. Unlike major excursions in the particle indices for this condensate stream, these minor excursions were detectable with a model PM 2500 particle monitor but not with a turbidimeter.

Whenever the level of particulate matter in a condensate flow stream causes the limiting particle index to be exceeded, condensate dumping is preferably achieved by using ball valves which open and close in response to electronic signals from a controller, subject to dead band control, actuated by the particle monitor when it measures a particle index corresponding to a limit within this dead band. Alternately, condensate dumping can be achieved by opening a manual valve in response to the sounding of an alarm actuated by the particle monitor.

Tests were conducted in which particle monitors were installed on a sample line of a condensate return system in each of three different industrial environments. These tests are described in the examples below.

EXAMPLE NO. 1

Installed on a sample line from the main condensate receiver in a Gulf Coast paper mill, a particle monitor logged particle indices minute by minute for several days. These particle indices were found to follow closely the total iron concentration. The latter was determined spectrophotometrically from grab samples taken periodically. This situation persisted even when condensate flow was increased dramatically to flush corrosion products from the condensate return system. Moreover, for concentrations above about 100 ppb, a linear relation between particle index and total iron was noted.

EXAMPLE NO. 2

Set up to monitor boiler feedwater at various points during its pretreatment, a particle monitor was used to find the cause of boiler tube fouling in an eastern United States steel mill. The particle monitor indicated breakthroughs and channelling were occurring in filters and zeolites downstream of hot process (hot lime) softeners, al lowing low level concentrations of particulate hardness to enter the normal boiler feedwater. Acidified feedwater hardness tests, run when the particle monitor registered these breakthroughs, revealed that the insoluble hardness levels were excessive (0.05 to 0.2 ppm, even though the soluble hardness levels were below detection limits.

EXAMPLE NO. 3

Tests were conducted using a particle monitor to identify those condensate streams in a northern United States paper mill that suffer the worst contamination during startups as well as those which do not pose a fouling threat. During the shutdown and startup of each condensate return system, the particle monitor was able to detect surges in the particle content of the condensate stream and easily track the duration of these surges, enabling the operator to determine when normal operating conditions had been achieved and then to return condensate to the boiler with confidence.

What is claimed is:

1. A method of controlling concentrations of particulate matter in condensate flow in a condensate return system, in which an intense light beam is directed towards a detector and across a portion of the condensate flow, concentrations of particulate matter in the condensate flow being controlled so that they do not exceed a predetermined limiting concentration, comprising:

(a) continuously measuring, on-line, numbers known as particle indices which are indicative of particulate matter concentrations in the condensate flow, each particle index being proportional to a ratio equal to fluctuations in intensity of the light beam divided by absolute intensity of the light beam, the fluctuations being caused by particles which are present in said portion of the condensate flow during a fixed interval of time; and (b) automatically diverting the condensate flow from the condensate return system when the particulate matter concentration, as indicated by the particle index, is greater than the predetermined limiting concentration.

2. The method according to claim 1 which further comprises directing said portion of the condensate flow through transparent vinyl tubing which is approximately 3 mm in inner diameter, the intense light beam being directed along a path generally perpendicularly to the direction of the condensate flow through the tubing and across said portion of the condensate flow.

* * * * *